US008734322B2

(12) United States Patent
Cordle

(10) Patent No.: US 8,734,322 B2
(45) Date of Patent: May 27, 2014

(54) VIBRATOR DEVICE

(76) Inventor: Joshua Damien Cordle, Rome, GA (US)

( * ) Notice: Subject to any disclaimer, the term of this patent is extended or adjusted under 35 U.S.C. 154(b) by 307 days.

(21) Appl. No.: 13/234,049

(22) Filed: Sep. 15, 2011

(65) Prior Publication Data

US 2012/0197072 A1 Aug. 2, 2012

Related U.S. Application Data

(60) Provisional application No. 61/462,340, filed on Feb. 2, 2011.

(51) Int. Cl.
*A61F 5/00* (2006.01)

(52) U.S. Cl.
USPC .......................................................... 600/38

(58) Field of Classification Search
USPC .................. 600/38; 128/845; 601/46, 40, 134
See application file for complete search history.

(56) References Cited

U.S. PATENT DOCUMENTS

| | | | | |
|---|---|---|---|---|
| 3,626,931 | A | 12/1971 | Bysakh | |
| 6,056,705 | A | 5/2000 | Stigar-Brown | |
| 6,179,775 | B1 | 1/2001 | Thompson | |
| 6,733,438 | B1 | 5/2004 | Dann | |
| 6,923,755 | B2 | 8/2005 | Norma | |
| 6,991,598 | B2 | 1/2006 | Klein | |
| 7,108,668 | B2 | 9/2006 | Fang | |
| 2005/0256369 | A1 * | 11/2005 | Gloth | 600/38 |
| 2007/0017528 | A1 | 1/2007 | Osterberg | |
| 2011/0071445 | A1 * | 3/2011 | Imboden et al. | 601/46 |

* cited by examiner

*Primary Examiner* — Christine Matthews

(57) ABSTRACT

A vibrator device to stimulate the clitoris of a user includes a vibrator mechanism, a sleeve to contain and align the vibrator mechanism, a stabilizer to support and locate the device, an elongated flexible strip to affix the device to the user, and a glove to couple vibration from the vibrator mechanism to the clitoris. The sleeve may form a pocket surrounding the vibrator mechanism. The strip may include two arms that provide extended area for attachment on either side of the vaginal orifice. The glove may be connected to one end of the sleeve so that, when the device is affixed to a user, the glove may be disposed in contact with the clitoris.

17 Claims, 5 Drawing Sheets

VIBRATOR DEVICE

CROSS REFERENCE TO RELATED APPLICATION

This application claims priority to U.S. Provisional Application Ser. No. 61/462,340 filed Feb. 2, 2011, the contents of which is incorporated by reference in its entirety.

BACKGROUND

The invention is in the field of adult sexual enhancement.

Some women enjoy constant clitoral stimulation during vaginal sex. Providing this can be awkward, uncomfortable, or inconvenient. Vibrator devices can provide clitoral stimulation, but prior art devices may interfere with vaginal sex, may fail to reliably direct vibration to the clitoris, or may include mounting devices that interfere with sexual enjoyment or potentially cause pain or injury.

Published US patent application 20070017528 to Osterberg describes a female condom with a supporting harness that may incorporate a vibratory element in a pocket within the wall of the condom. The supporting harness, as well as the condom itself may impair comfort or sensations from vaginal intercourse.

U.S. Pat. No. 6,923,755 to Norma describes a spring-loaded clip intended to grasp labial tissues to position a vibrator mechanism. The spring-loaded clip is presumably designed to provide sufficient holding force to retain the vibrator in position, but less force than that which might produce discomfort or injury. The variation of anatomy and sensitivity between women and between different stages of sexual arousal may limit an effective but tolerable grasping force to a subset of women and times.

U.S. Pat. No. 6,733,438 to Dann describes a device designed to attach to the clitoral region by suction. The patent describes topical drug delivery by the suction device. The small size of the described device is consistent with the weak holding power of suction-based devices and inconsistent with the larger mass of vibration mechanisms.

U.S. Pat. No. 7,108,668 to Fang describes a cylindrical vibrator enclosed in a snap-together housing including flexible connections between a switch, batteries, and a motor disposed in the housing. The described device is freestanding. There is no description of disposing the device proximate targeted anatomy.

U.S. Pat. No. 6,991,598 to Klein describes a vibrator attached to clothing by magnetic or other fasteners. The patent does not teach a fixed alignment of the vibrator to anatomical features. The use of clothing and fasteners may interfere with vaginal intercourse or with continued proximate placement between the vibrator and targeted anatomy.

U.S. Pat. No. 6,179,775 to Thompson describes a pad device with hydrophilic adhesive designed to adhere within the vulval vestibule and support the clitoris in a more upright position and to transmit motion of a penis moving within the vagina to the clitoris. The device relies on the intermittent relative motion of the penis and the pad and does not provide vibratory stimulation at all times during vaginal intercourse.

U.S. Pat. No. 6,056,705 to Stigar-Brown describes a locking plier-like clamp with an included vibratory mechanism. The spring-loaded clamp locks into position over the clitoris and may be released by turning clamping screws. The freely depending handles of the clamp may interfere with comfortable vaginal intercourse. The user must use care to turn the clamping screws in the proper direction to avoid tightening the clamp when attempting to release it from the clitoris.

U.S. Pat. No. 3,626,931 to Bysakh describes an open ended device in the form of a truncated cone disposed over the vaginal orifice and designed to engage with an inserted penis. An extension on the device engages a remote vibrator. The patented device apparently moves with the penis and only intermittently engages and stimulates female anatomical targets. The described device includes bulky external parts and includes no features for directing vibration to a particular location.

Each of these described prior art devices may be awkward, uncomfortable, or inconvenient. Some devices fail to provide reliably directed continuous stimulation to the clitoris during vaginal intercourse. For females that require constant external clitoral stimulation to reach climax, none of the above are consistently useful. Some may provide the needed stimulation but reduce the sexual partner's pleasure and do not allow the full sexual experience for both partners at the same time. A true intimacy enhancer should be easy to use, effectively stimulate the desired area causing the wearer to reach climax and allow the act of intercourse to take place comfortably. Another object of the invention is to provide a stimulatory device that provides constant external stimulation to the female clitoris through constant hands-free contact of a vibrating device with the clitoris. It is also an objective of this invention to provide the user with constant clitoral stimulation through the use of a device which adheres to the exterior genitalia in a way that ensures correct positioning and constant contact with the target area.

It is another object of the invention to provide a hygienic means of providing clitoral stimulation. Yet another object of the invention to ensure that the user is comfortable and feels natural during use of the device in conjunction with the act of intercourse or penetration in most conceivable positions. Another object of the invention is to provide a device which is inexpensive to manufacture and limited in number of uses of the encapsulated motor to ensure optimum effectiveness. A still further object of the invention is to facilitate enhanced intimacy between partners by allowing each partner to freely use both hands and experience orgasm without the need to focus on effective use of the stimulation device.

SUMMARY

In some embodiments, the invention includes a vibrator device to stimulate the clitoris of a user including a vibrator mechanism, a sleeve to contain and align the vibrator mechanism, a stabilizer to support and locate the device, an elongated flexible strip to affix the device to the user, and a glove to couple vibration from the vibrator mechanism to the clitoris. The sleeve may form a pocket surrounding the vibrator mechanism. The strip may include a first end and a second end, with the first end bifurcated into two arms that provide extended area for attachment on either side of the vaginal orifice. Both the sleeve and the stabilizer may be attached to the strip. The glove may be connected to one end of the sleeve so that, when the device is affixed to a user, the glove may be disposed in contact with the clitoris.

In some embodiments, the strip may include substantially planar opposite surfaces with a first surface disposed in partial contact with the user. Portions of this surface may have adhesive properties or materials to hold the strip in place during use. The strip may comprise a hydrocolloid or other viscoelastic gel.

The stabilizer may connect to the same first surface of the strip and may include one or more substantially rectangular bodies extending parallel to the long axis of the strip. These bodies may serve to mechanically isolate the sleeve from the vulval vestibule so that more of the vibratory energy may be focused onto the clitoris.

In some embodiments, the sleeve may be a hollow elongated body with a base and an apex at opposite ends and a connection region between the base and the apex. The glove may connect to the sleeve at the apex, with the strip connected to the connection region. The vibrator mechanism may be disposed within the hollow body of the sleeve and may include an activating switch. The switch may align with the sleeve base and may extend through an opening in the base or may be actuated through the flexible material of the base.

The glove may extend from the sleeve apex and, in some embodiments, may include compliant walls and a terminal involution that cups the clitoris.

In some embodiments, the connection region of the sleeve connects to the strip through a flexible connection that disposes the apex and the base on opposite sides of the strip with the apex disposed proximate the first surface and the base disposed proximate the second surface. The connection also orients the apex of the sleeve towards the second end of the strip and the base of the sleeve towards the bifurcated first end of the strip.

In some embodiments, the invention comprises a hydrocolloid device to attach a vibratory mechanism to the body of a user, where the device includes features that encapsulate, support, and target the vibratory mechanism to transmit vibration to the clitoris of a user.

In other embodiments, the invention includes a device to apply vibration from a vibratory mechanism to the clitoris of a user, including a hollow sleeve to contain the vibratory mechanism, an elongated flexible strip to affix the device to the user, a stabilizer to support and locate the device, and a glove to couple vibration from the vibrator mechanism to the clitoris. The glove may be connected to the apical end of the sleeve proximate the inner side of the strip. The glove may include compliant walls and a terminal involution to cup the clitoris.

The strip may include an adhesive inner side and may be attached to the sleeve via a flexible connection that disposes the sleeve at an angle with respect to the plane of the strip with the stabilizer attached to the inner side. The glove may be configured to transmit vibration from the vibratory mechanism to the clitoris when the vibratory mechanism is disposed within the sleeve and when the device is affixed to a user.

In some embodiments, the sleeve may include an opening through which the vibratory mechanism may be inserted and removed to support replacement of either the vibratory mechanism or of the device itself. The opening may be disposed on the end of the sleeve opposite the apical end, and may have a closed position and an open position, where the opening in the open position permits insertion or removal of the vibratory mechanism, and the opening in the closed position retains the vibratory mechanism and protects the vibratory mechanism against infiltration of fluids.

The opening may provide access to an actuator switch in the vibratory mechanism. This access may be through a wall of the sleeve.

The glove further may include compliant walls disposed intermediate the apical end of the sleeve and the terminal involution configured to apply a force to retain the terminal involution proximate the clitoris.

In some embodiments, the stabilizer may include first and second supports disposed substantially parallel to the long axis of the strip. The supports may serve to bias a portion of the inner side away from the user and thereby prevent damping of the motion produced by the vibratory mechanism so that more of the vibratory motion may be coupled through the glove to the clitoris.

DETAILED DESCRIPTION

The invention is intended to be affixed to the body of a woman. The inner surface of the device is that surface proximate the body. The outer surface is that surface opposite the inner surface and facing away from the body.

Figure 1:
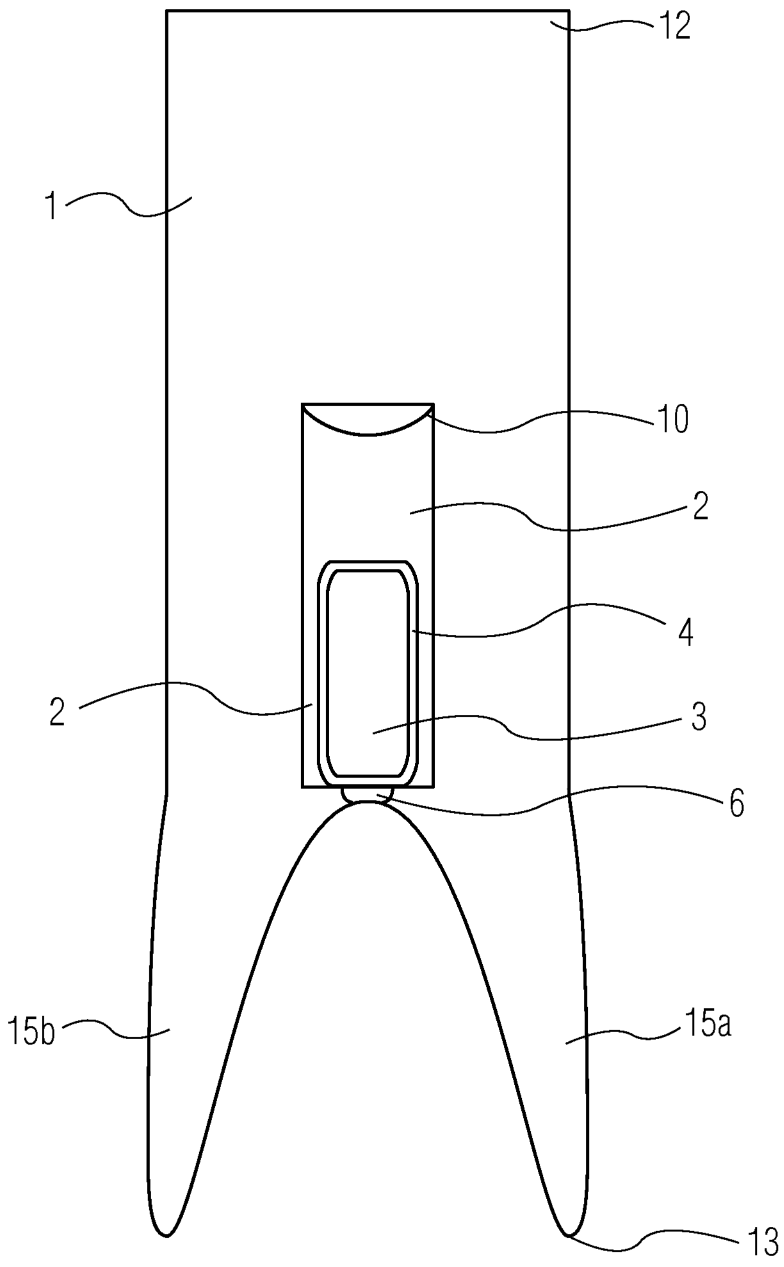
FIG. 1 shows a plan view of an embodiment of the device of the invention from the outer surface.
Figure 2:
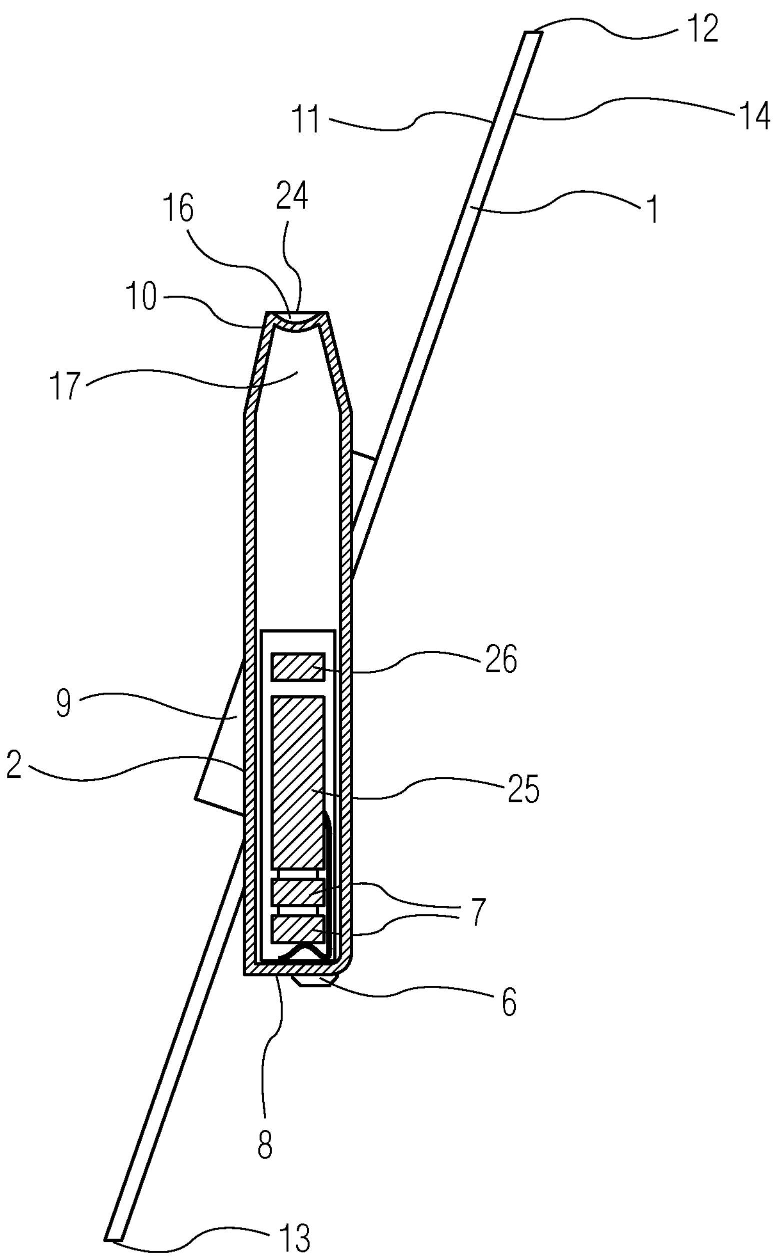
FIG. 2 shows a partial side sectional view of an embodiment of the device of the invention parallel to the long axis of the strip.
Figure 3:
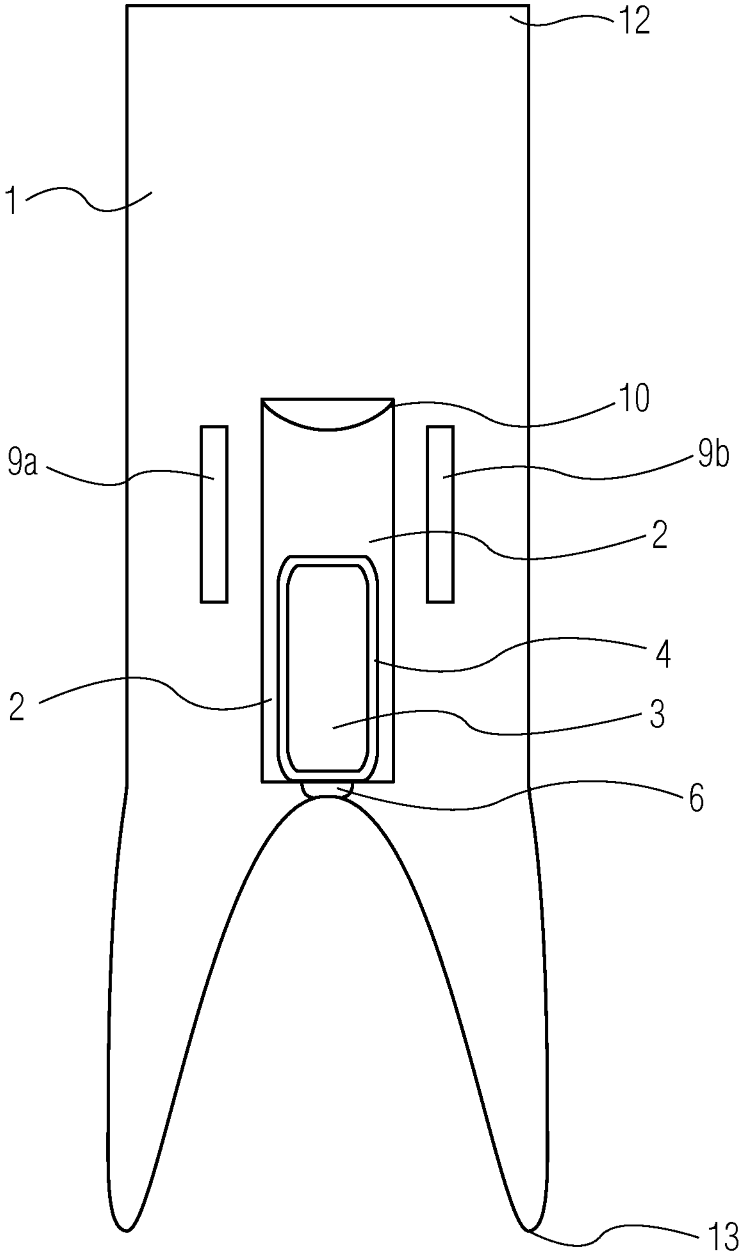
FIG. 3 shows a plan view of an embodiment of the device of the invention from the inner surface.

FIGS. 1-3 show views of an embodiment of the invention with like numbers indicating the same part. The function of the device is to apply continuous clitoral stimulation in the form of mechanical vibration. The embodiment includes major parts of a vibrator mechanism 3, a sleeve 2, a stabilizer 9, a strip 1 and a glove 10.

Vibrator mechanism 3 generates mechanical vibration. Vibrator mechanisms are well known in the art. In some embodiments, vibrator mechanism 3 may include a housing (best seen in FIG. 3), a power source (not shown), a vibrator (not shown), and a switch 6. The housing may be a substantially closed plastic or metal enclosure that surrounds and contains the other components. The housing may include a rigid shell.

The power source may be an electrical storage device such as a battery. Other power storage devices, such as wound springs may also be applicable. FIG. 2 shows sleeve 2 illustrated as if transparent to reveal one embodiment of the placement of the components of vibrator mechanism 3 (respectively from the bottom of the drawing: switch 6, batteries 7, motor 25, and vibrator mass 26) surrounded by a housing and capped by glove 10. Vibrators may include motors, such as electrical motors, coupled to the power source. The vibrator may also include a vibration mass, such as a collar eccentrically mounted on a motor shaft. The housing may also or alternatively serve as a vibration mass. In some embodiments, vibrator mechanism 3 may resemble that disclosed in U.S. Pat. No. 7,108,668 to Fang, which is incorporated by reference in its entirety.

Switch 6 controls operation of vibrator mechanism 3. Switch 6 may directly actuate vibrator mechanism 3 by connecting the power source to the motor. Alternatively, switch 6 may indirectly actuate vibrator mechanism 3 through a controller that connects the power source to the motor. Switch 6 may be an electrical slide switch. Alternatively, switch 6 may be an alternate action push button switch or a simple push button switch. Electrical slide switches and alternate action push button switches advantageously indicate the state of the switch from their position. Switch 6 may protrude beyond the housing so that a user may activate switch 6 without opening the housing.

Sleeve 2 contains and aligns vibrator mechanism 3. In some embodiments sleeve 2 is an elongated hollow body with a cavity 4. Sleeve 2 extends from basal end (or base) 8 to the glove 10 connected at the apical end (or apex) 24 opposite basal end 8. Sleeve 2 may connect to strip 1 in a manner described in more detail below. Sleeve 2 may be composed of a fluid impermeable flexible material such as a hydrocolloid or other polymer gel.

Cavity 4 is sized to fit vibrator mechanism 3. In some embodiments, cavity 4 may be slightly smaller than vibrator mechanism 3 so that cavity 4 stretches to accommodate the inserted vibrator mechanism 3. The restoring force from the stretched cavity 4 may serve to keep vibrator mechanism 3 in a desired position within cavity 4 and may serve to tightly couple vibrations produced by vibration mechanism 3 to the body of sleeve 2.

The device may be sized to fit the anatomy of the user. In some embodiments, strip 1 may be about 1.5 inches wide and may be from about 3 inches to about 4 inches long. Sleeve 2 may be about 0.75 inch in diameter and may be about 1.25 inches in length.

In some embodiments, sleeve 2 may include an opening (not shown) at or near basal end 8. The vibratory mechanism may be inserted and removed through the opening to support replacement or servicing of either vibratory mechanism 3 or of the balance of the device. The opening may be disposed at any position in sleeve 2, but in some embodiments is disposed on the basal end 8 of sleeve 2. The opening may have a closed position and an open position, where the opening in the open position permits insertion or removal of vibratory mechanism 3, and the opening in the closed position retains vibratory mechanism 3 and protects vibratory mechanism 3 against infiltration of fluids. The opening may be closed by adhesive portions of the wall of sleeve 2 proximate the opening. The opening may provide access to switch 6 in vibratory mechanism 3. The access may be through a wall of sleeve 2, (such as through the opening in the closed position) or through the opening.

Stabilizer 9 supports and locates the device. In some embodiments, stabilizer 9 may include at least one support 9*a*. In some embodiments, first and second supports 9*a* and 9*b* may be disposed on the inner surface 11 of strip 1 and substantially parallel to the long axis of strip 1. Supports 9*a* and 9*b* may serve to bias a portion of the inner side of strip 1 and attached sleeve 2 away from the user and thereby reduce damping of the motion produced by vibrator mechanism 3.

In some embodiments, supports 9*a* and 9*b* may be substantially rectangular supports disposed on either side of sleeve 2. Supports 9*a* and 9*b* may form ribs of approximately square cross section that locally impart some rigidity to the pliant strip 1. These relatively rigid supports, while still flexible enough to conform to curving anatomical surfaces, serve to bias a portion of the inner side of strip 1 away from the user. This may serve to prevent direct contact of sleeve 2 to the user. Isolating sleeve 2 in this manner reduces damping of the motion produced by vibrator mechanism 3 so that more of the vibratory motion may be coupled through glove 10 to the clitoris.

Strip 1 affixes the device to the user and serves to connect the several parts of the device. Strip 1 may be an elongated and substantially planar body with upper end 12 and lower end 13. Strip 1 may be pliant and flexible to conform to curving anatomical surfaces. Strip 1 includes an adhesive inner surface 11 and a non-adhesive opposing surface 14. Adhesive material may be disposed over only a portion of the inner surface 11 so as to prevent unwanted adhesion to body surfaces, particularly in the area adjacent sleeve 2 for the reasons mentioned above. Strip 1 may be composed of a fluid impermeable flexible material such as a hydrocolloid or other polymer gel or elastomer. In some embodiments, strip 1 may include multiple layers of materials to provide the appropriate mix of properties. For example, strip 1 may include a hydrocolloid layer and an adhesive layer.

Strip 1 may be attached to sleeve 2 via a flexible connection that disposes sleeve 2 at an angle with respect to the plane of strip 1. In some embodiments, sleeve 2 includes a connection region intermediate basal end 8 and apical end 24. Sleeve 2 may connect to strip 1 through a flexible connection that connects the connection region of sleeve 2 to strip 1 approximately midway up the length of strip 1. The flexible connection may align sleeve 2 at an angle with respect to the plane of strip 1. This angle serves to position glove 10 (connected to the apex of sleeve 2) proximate the clitoris when strip 1 adheres to the vulval vestibule and to adjacent anatomical features. The angle disposes the apex and the base on opposite sides of the strip with the apex disposed proximate the inner surface and the base disposed proximate the outer surface. The connection also orients the apex of sleeve 2 towards the second end of strip 1 and the base of sleeve 2 towards the bifurcated first end of strip 1. The angled connection also advantageously disposes switch 6 on the basal end 8 of sleeve 2 to a position more readily reached with the device installed. The device may thus be activated or deactivated without concern for dislodging the strip.

In some embodiments, the flexible connection between sleeve 2 and strip 1 may include a connection completely around sleeve 2. Strip 1 may be visualized as a brim extending outward from sleeve 1 and disposed at an angle with respect to the long axis of sleeve 2. Sleeve 2 thus penetrates strip 1 and joins to it along the substantially elliptical intersection between sleeve 2 and strip 1. In other embodiments, strip 1 and sleeve 2 may be formed as two separate pieces. In such embodiments, strip 1 may include a substantially elliptical hole disposed on or near the midline of strip 1 and oriented with major axis parallel to the midline of strip 1. Sleeve 2 may include a projecting brim extending a substantially constant distance from the cylindrical body of sleeve 2 and disposed at an angle with respect to the long axis of sleeve 2, thus forming a substantially elliptical boss of relatively thin cross section about sleeve 2. The body of sleeve 2 may insert into the hole in strip 1 so that the boss contacts one surface of strip 1. This boss may adhere to strip 1 to dispose sleeve 2 in proper orientation with respect to strip 1. The boss may extend about $\frac{3}{16}$ inch from the body of sleeve 2.

Figure 5:
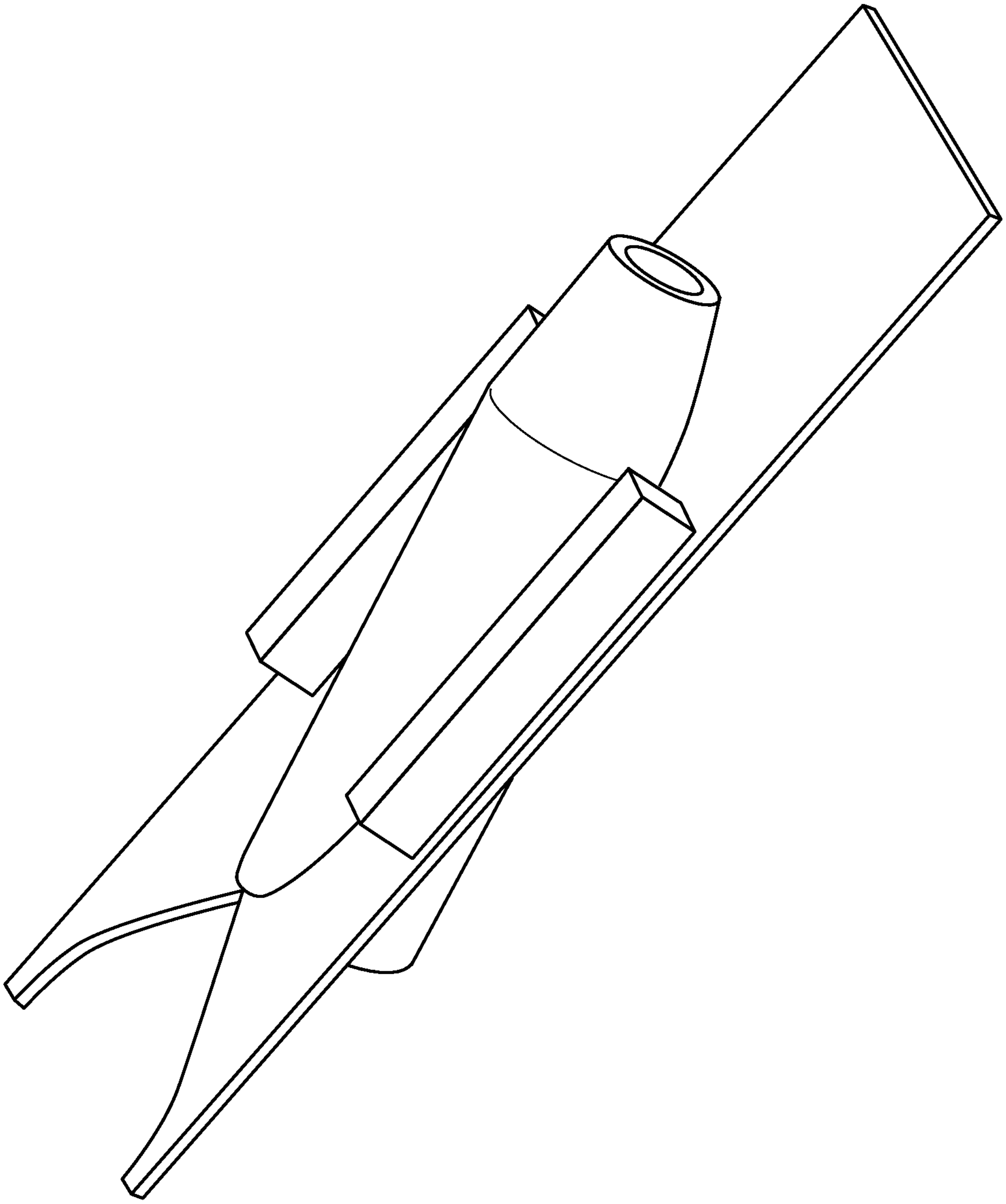
FIG. 5 shows an isometric view of an embodiment of the device of the invention.

Sleeve 2 may be disposed at an acute angle with respect to strip 1. In some embodiments, the angle may be in the range of about 2 degrees to about 30 degrees to best dispose the switch outwards of the outer surface of strip 1, to dispose the glove inward of the inner surface of strip 1, when the device is mounted on a woman. In other embodiments the acute angle may be about 10 degrees to about 20 degrees. FIG. 5 shows the angled disposition of sleeve 2 with respect to strip 1 (labels omitted for clarity).

In some embodiments strip 1 includes a bifurcation partway toward lower end 13 so that strip 1 continues below the bifurcation as a pair of separated arms 15*a* and 15*b*. Arms 15*a* and 15*b* may be advantageously sized to permit disposition on either side of the vaginal orifice, thus extending the surface and forces adhering strip 1 to the body, while permitting unhindered access for vaginal penetration.

Glove 10 couples vibration from vibrator mechanism 3 to the clitoris. Glove 10 may be disposed as a continuation of sleeve 2 from the apical end. Glove 10 may include terminal involution 16 at its distal end and compliant walls 17 intermediate sleeve 2 and terminal involution 16. Involution 16 forms a closed end cavity sized to cup the clitoris so that vibrational motion from vibrator mechanism 3 may couple into the clitoris. Involution 16 forms a concave receptacle that may increase or decrease in size as more or less of compliant walls 17 reflect inwardly. Compliant walls 17 may be configured to apply a force between the apical end of sleeve 2 (indirectly anchored to the vulval vestibule through its connection to strip 1) and involution 16 to retain terminal involution 16 proximate the clitoris. Glove 10 may thus transmit vibration from vibratory mechanism 3 to the clitoris when vibratory mechanism 3 is disposed within sleeve 2 and when the device is affixed to a user.

In some embodiments, compliant walls 17 may taper from above the apical end of sleeve 2 (sized to fit vibrator mechanism 3) to better fit a user's anatomy.

While each of strip 1, stabilizer 9, sleeve 2, and glove 10 may be formed as separate parts subsequently attached together, in some embodiments, these parts may be molded or cast as a common assembly. If formed as separate parts, the components may be affixed to one another using adhesives, fasteners, stitching, or any of a number of methods known in the art.

Parts may be formed of hydrocolloid or other polymer gel or of soft plastic or soft rubber or any other material that does not irritate the skin. Suitable materials include phthalate-free thermoplastic elastomers such as those distributed by Topco Sales of Chatsworth, Calif. The adhesive material must be suited for human skin and be strong enough to hold the device in place against light friction but not too strong as to cause irritation during removal. Some embodiments may include materials, such as hydrocolloid or other polymer gels that intrinsically adhere to tissue. Adherence of such materials may be modulated by changing the smoothness of the device surface finish. Other embodiments include applied adhesive. In any case, the adhesive must also hold when introduced to moisture and when wet. Suitable adhesive materials may include "Soft Skin Adhesive" brand of silicone elastomer distributed by Dow Corning Corporation. The adhesion advantage of the hydrocolloid strip eliminates the need for straps or other mounting hardware.

In some embodiments, only selected portions of the device include adhesive properties. Adhesive portions include inner surface 11 of strip 1 (including arms 15*a* and 15*b*) except those portions of strip 1 disposed proximal to supports 9*a* and 9*b*. Adhesive portions may also include the surfaces of supports 9*a* and 9*b* disposed distal to inner surface 11. This disposition of adhesive surfaces firmly attaches the device but also isolates sleeve 2 to prevent damping of vibration that might occur if sleeve 2 were immobilized.

In some embodiments, the device includes vibrator mechanism 3 as an integral part. In other embodiments, vibrator mechanism 3 may be supplied separately so that the vibrator mechanism may be reused with a fresh support and attachment device for improved hygiene and economy.

Figure 4:
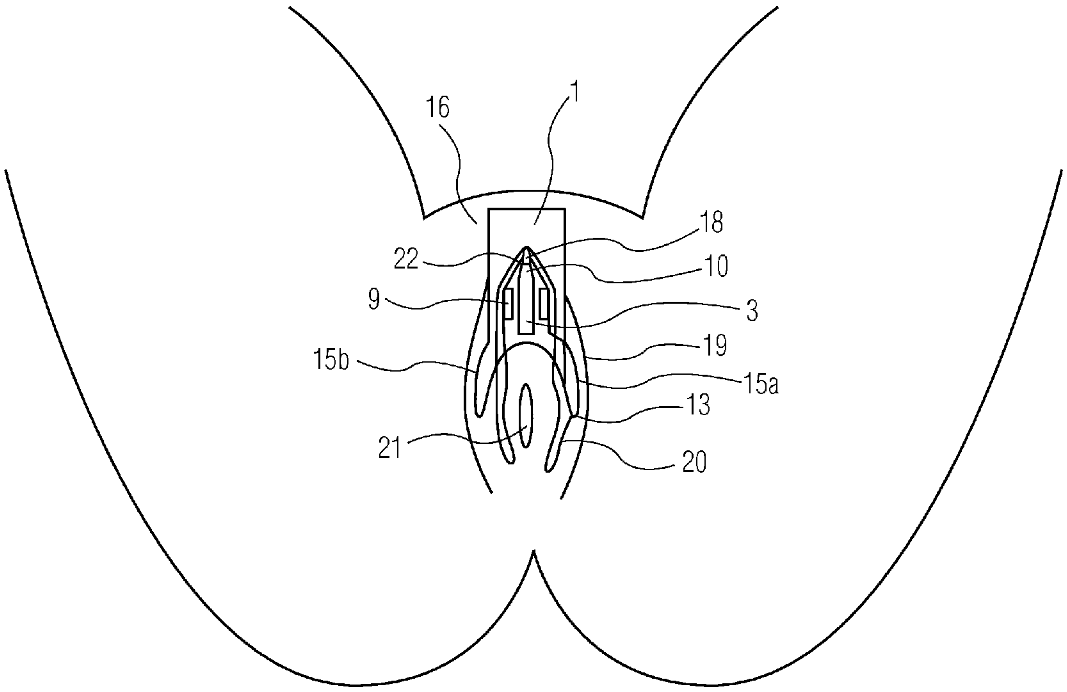
FIG. 4 shows attachment of an embodiment of the device of the invention to the body of a user.

FIG. 4 illustrates the proper placement of the device on a user. Strip 1 is illustrated as if transparent to reveal the disposition of structures beneath. The unique shape of the arms 15*a* and 15*b* disposed proximate lower end 13 allow unobstructed access to the vaginal opening 21 and conform comfortably to the contours of labia majora 19. Pliable sleeve 2 is capped by glove 10 shown in relation to clitoris 18. Stabilization supports 9*a* and 9*b* make contact with the user's body just below clitoris 18 and inside labia minora 20 resulting in the separation of both clitoral hood 22 and labia minora 20 and exposing clitoris 18 for increased contact with glove 10 at the tip of sleeve 2. Arms 15*a* and 15*b* are shown adhered between the labia majora 19 and the labia minora 20 in a manner which allows unobstructed access to the vaginal opening 21 whereby allowing intercourse or penetration to take place. The upper end 12 of the strip 1 is attached to mons pubis 23 which should be free of pubic hair to ensure proper adhesion.

The device of the invention is intended to stimulate the clitoris during vaginal intercourse. This stimulation occurs without the need for either partner to hold the device in place; the device holds itself in place allowing the partners to continue as though no device were present. To attach the device, a user first pulls away a release liner to expose the adhesive side of strip 1. She then orients upper end 12 upwards then places glove 10 snugly against her clitoris. As she pulls in down against her clitoris, pliable glove 10 yields into itself slightly. Compliant walls 17 provide an elastic restoring force that maintains firm contact of terminal involution 16 of glove 10 against the clitoris. The user then places the adhesive side of strip 1 against her skin at the mons pubis 23 and in the area between the labia majora 19 and the labia minora 20 as shown in FIG. 4. Once the device is securely in place all that is exposed on the outside is the soft top surface of strip 1, the top of sleeve 2, and switch 6. Each of these exposed parts are composed of or encased within a soft pliable material. At any point a user may activate or deactivate switch 6 (as by sliding a slide switch in some embodiments) to start or stop the vibrator. The device provides a constant external stimulation for the user in a non cumbersome way without either partner needing to focus on the external stimulation. The stimulation may increase natural lubrication which can help prevent irritation from sexual intercourse and may also help a woman reach climax during vaginal sexual intercourse.

Although the above description discloses various aspects of the invention with reference to particular embodiments, it should be understood that any of the features, functions, materials, or construction details may be combined with any other of the described features, functions, materials, or construction details. The scope of the invention is not limited to those described embodiments but includes such equivalents as would be apparent to a person skilled in the art upon reading this disclosure.

I claim:

1. A vibrator device to stimulate a clitoris of a user having a vaginal orifice, the device comprising:
- a vibrator mechanism;
- a sleeve to contain and align the vibrator mechanism, the sleeve surrounding the vibrator mechanism;
- an elongated flexible strip to affix the device to the user, the strip including a first end and a second end, the first end bifurcated into a first arm and a second arm, the strip attached to the sleeve;
- a stabilizer to support and locate the device, the stabilizer attached to the strip; and
- a glove to couple vibration from the vibrator mechanism to the clitoris, the glove connected to the sleeve,
- wherein, when the device is affixed to a user, the first arm and the second arm are configured to dispose on either side of the vaginal orifice and the glove is configured to dispose in contact with the clitoris,
- wherein the sleeve includes an elongated hollow body, a base and an apex at opposite ends of the hollow body, and a connection region intermediate the base and the apex, the glove connected to the apex, and the strip connected to the connection region, and
- wherein the glove includes compliant walls and a terminal involution, the walls extending from the apex to the terminal involution wherein, when the device is affixed to a user, the terminal involution is configured to cup the clitoris.

2. The device of claim 1 wherein the connection region connects to the strip through a flexible connection that disposes the apex and the base on opposite sides of the strip, the apex disposed proximate a first surface of the strip and the second end.

3. A method of applying vibration to the clitoris of a woman, the method comprising:

providing the vibrator device of claim 1;

applying the vibrator device with the first arm and the second arm disposed on either side of the vaginal orifice and the glove disposed in contact with the clitoris; and activating the vibrator mechanism.

4. The method of claim 3 further comprising removing and replacing the vibrator mechanism within the sleeve.

5. The device of claim 1 wherein the strip further includes a first substantially planar surface and a second surface opposed to the first surface, and wherein the stabilizer is attached to the first surface.

6. The device of claim 5 wherein the strip further includes an adhesive material disposed on a portion of the first surface.

7. The device of claim 6 wherein the strip includes a hydrocolloid material.

8. The device of claim 7 wherein the stabilizer includes a first substantially rectangular support disposed parallel to a long axis of the strip.

9. The device of claim 1 wherein the stabilizer further includes a second support disposed parallel to a first support.

10. The device of claim 1 wherein the vibrator mechanism includes a switch, the vibrator mechanism disposed within the hollow body and the switch disposed proximate the base.

11. A device to apply vibration from a vibratory mechanism to a clitoris of a user, the device comprising:

a hollow sleeve to contain the vibratory mechanism;

an elongated flexible strip to affix the device to the user, the strip defining an included plane and including an adhesive inner side, the strip attached to the sleeve via a flexible connection that disposes the sleeve at an angle with respect to a plane of the strip;

a stabilizer to support and locate the device, the stabilizer attached to the inner side; and a glove to couple vibration from the vibratory mechanism to the clitoris, the glove connected to the sleeve, wherein, when the vibratory mechanism is disposed within the sleeve and the device is affixed to a user, the glove is configured to transmit vibration from the vibratory mechanism to the clitoris, and wherein the glove includes a terminal involution, the glove extending from an apical end of the sleeve disposed proximate the inner side wherein, when the device is affixed to a user, the terminal involution is configured to cup the clitoris.

12. The device of claim 11 wherein the sleeve includes an opening through which the vibratory mechanism may be inserted and removed.

13. The device of claim 12 wherein the opening is disposed on an end of the sleeve opposite the apical end, and wherein the opening has a closed position and an open position, the opening in the open position permitting insertion or removal of the vibratory mechanism, the opening in the closed position retaining the vibratory mechanism and protecting the vibratory mechanism against infiltration of fluids.

14. The device of claim 13 wherein the opening provides access to an actuator switch in the vibratory mechanism.

15. The device of claim 14 wherein the glove further includes compliant walls disposed intermediate the apical end of the sleeve and the terminal involution, wherein, when the device is affixed to a user, the compliant walls are configured to apply a force to retain the terminal involution proximate the clitoris.

16. The device of claim 15 wherein the stabilizer includes first and second supports disposed substantially parallel to a long axis of the strip, wherein, when the device is affixed to a user, the supports bias a portion of the inner side away from the user.

17. The device of claim 16 wherein the flexible connection includes a substantially elliptical junction between the sleeve and the strip.

* * * * *